United States Patent
Benedek et al.

(10) Patent No.: US 8,388,900 B2
(45) Date of Patent: Mar. 5, 2013

(54) APPARATUS AND METHOD FOR TREATING IMPURITIES IN AIR AND MATERIALS

(75) Inventors: Karen Benedek, Winchester, MA (US); Philip C. Carbone, North Reading, MA (US); Derek Affonce, Foxborough, MA (US)

(73) Assignee: Primaira, LLC, Woburn, MA (US)

(*) Notice: Subject to any disclaimer, the term of this patent is extended or adjusted under 35 U.S.C. 154(b) by 591 days.

(21) Appl. No.: 12/587,948

(22) Filed: Oct. 14, 2009

(65) Prior Publication Data

US 2010/0158749 A1 Jun. 24, 2010

Related U.S. Application Data

(63) Continuation-in-part of application No. 12/312,690, filed on May 21, 2009, now Pat. No. 8,114,358.

(51) Int. Cl.
*A61L 9/00* (2006.01)
*A61L 2/00* (2006.01)
*A62B 7/08* (2006.01)
*B03C 3/00* (2006.01)

(52) U.S. Cl. ........ 422/186.07; 422/1; 422/3; 422/5; 422/22; 422/24; 422/121; 422/123; 95/57; 95/226

(58) Field of Classification Search ........... 422/1, 3, 422/5, 22, 24, 121, 123, 186.07, 306; 95/57, 95/226; 96/224
See application file for complete search history.

(56) References Cited

U.S. PATENT DOCUMENTS

| | | | |
|---|---|---|---|
| 4,343,765 A * | 8/1982 | Elston et al. .......... 422/3 |
| 4,904,289 A | 2/1990 | Miyakami et al. | |
| 4,990,311 A * | 2/1991 | Hirai et al. .......... 422/4 |
| 5,015,442 A * | 5/1991 | Hirai ................ 422/121 |
| 5,152,077 A | 10/1992 | Liang | |
| 5,230,220 A | 7/1993 | Kang et al. | |
| 5,369,892 A | 12/1994 | Dhaemers | |
| 6,134,806 A | 10/2000 | Dhaemers | |
| 6,391,272 B1 | 5/2002 | Schroeder | |
| 6,845,569 B1 | 1/2005 | Kim | |
| 2002/0139124 A1 | 10/2002 | Palermo | |
| 2004/0003511 A1 | 1/2004 | Silver | |
| 2004/0146437 A1 | 7/2004 | Arts et al. | |
| 2004/0161371 A1 | 8/2004 | Russell et al. | |
| 2005/0089458 A1 | 4/2005 | Oke | |
| 2006/0104858 A1 | 5/2006 | Potember et al. | |
| 2008/0118395 A1 | 5/2008 | Benedek | |

FOREIGN PATENT DOCUMENTS

| | | |
|---|---|---|
| DE | 36 37 702 A1 | 5/1988 |
| EP | 0 269 941 | 6/1988 |
| JP | 2002-263181 | 9/2002 |
| JP | 2005-226861 | 8/2005 |
| WO | WO 90/02572 | 3/1990 |
| WO | WO 03/080375 | 10/2003 |
| WO | WO 2008/103719 A1 | 8/2008 |
| WO | WO 2008/127315 A2 | 10/2008 |

* cited by examiner

*Primary Examiner* — Jill Warden
*Assistant Examiner* — Monzer Chorbaji
(74) *Attorney, Agent, or Firm* — Pauley Petersen & Erickson

(57) ABSTRACT

An assembly and method for treating or otherwise improving an atmosphere contained within an enclosed space. The enclosed space can be a container such as a bag or other housing for equipment, food and/or suitable material. Ozone is generated within an atmosphere that is exposed to the material. The generated ozone is mixed with the atmosphere. At least a portion of the generated ozone is then removed from the mixed atmosphere. The assembly and method can be used to treat contaminated sports equipment and the like, as well as to treat food storage atmospheres, such as those exposed to fresh fruits and vegetables.

29 Claims, 18 Drawing Sheets

| Lamp Catalog Number | | Nominal Lamp Length | Lamp Watts | Approximate Lamp Current mA | Ultraviolet Output | | Ozone Output | Rated Effective Life (hrs) |
|---|---|---|---|---|---|---|---|---|
| Ozone Free | Ozone Producing | | | | Total Watts | Microwatts @ 1 meter | | |
| G18T6L/U | G18T6VH/U | 8-1/4" | 17 | 425 | 5.8 | 59 | 1.6 | 10,000 |
| G24T6L/U | G24T6VH/U | 11-1/4" | 25 | 425 | 8.5 | 82 | 2.3 | 10,000 |
| G30T6L/U | G30T6VH/U | 14-1/4" | 32 | 425 | 11.2 | 101 | 3.0 | 10,000 |
| G36T6L/U | G36T6VH/U | 17-1/4" | 39 | 425 | 13.8 | 120 | 3.7 | 10,000 |
| G48T6L/U | G48T6VH/U | 23-1/4" | 50 | 425 | 19.3 | 164 | 5.2 | 10,000 |

FIG.8

| Common Name | Ethylene Production | Ethylene Sensitivity |
|---|---|---|
| Apple | Very High (>100µl/kg-hr) | Highly Sensitive |
| Banana | Moderate (1-10µl/kg-hr) | Highly Sensitive |
| Broccoli | Very Low (<0.1µl/kg-hr) | Highly Sensitive |
| Citrus (oranges) | Very Low (<0.1µl/kg-hr) | Moderately Sensitive |
| Pears | High (10-100µl/kg-hr) | Highly Sensitive |
| Tomatoes (ripe) | Very Low (<0.1µl/kg-hr) | Highly Sensitive |
| Tomatoes (unripe) | High (10-100µl/kg-hr) | Low Sensitive |

FIG.9

| Known Ethylene Control Technology | Limitation for Transport and Storage Applications |
|---|---|
| Ventilation | Refrigerated shipping containers and storage facilities or devices are not designed for significant ventilation due to energy requirements to condition outside air, risk of contamination, risk of drying-out the fruit and vegetables, and difficulty ventilating individual cartons of fresh fruit and vegetables (FF&V) |
| Potassium Permanginate ($KMnO_4$) (absorption/catalytic oxidation of $C_2H_4$ to $H_2O$ and $CO_2$) | One-time use, this produce poses an environmental and cost burden due to the need to dispose of the $KMnO_4$ as a hazardous waste |
| Bromated Carbon (absorbent) | Costly and waste products must be disposed |
| Catalytic Oxidizers (e.g. $TiO_2$ photocatalytic oxidation, $C_2H_4$ to $H_2O$ and $CO_2$) | High pressure drop of catalytic reactor leads to excessive power requirement for air-flow through the reactor, it is difficult to draw the air out of individual FF&V shipping cartons to be cleaned, and long residence times required for significant ethylene reduction effectiveness results in an excessively large system. |

FIG.10

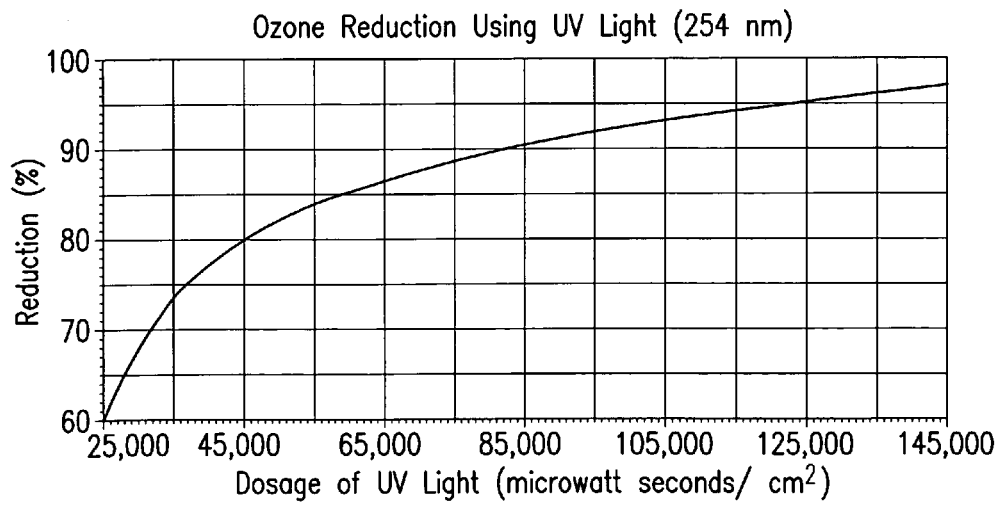

FIG.11

APPARATUS AND METHOD FOR TREATING IMPURITIES IN AIR AND MATERIALS

CROSS REFERENCE TO RELATED APPLICATION(S)

This Patent application is a continuation-in-part of U.S. patent application Ser. No. 12/312,690 with an international filing date of May 21, 2009 now U.S. Pat. No. 8,114,358. The parent application is hereby incorporated by reference herein in its entirety and is made a part hereof, including but not limited to those portions which specifically appear hereinafter.

GOVERNMENT INTEREST

This invention was made with government support under DOD Contract Numbers W911QY-07-C-0005 and W911QY-07-CO117, respectively. The United States Government has certain rights in the invention as provided in the respective contracts.

BACKGROUND OF THE INVENTION

1. Field of the Invention

This invention relates generally to materials, apparatuses, assemblies and methods for treating air such as by removing one or more impurities from the air.

In one aspect, the invention relates to a material and/or air cleaning apparatus and a method for removing impurities from the air, resulting in air that has been deodorized, dried, sanitized, treated, modified, improved and/or otherwise cleaned of undesired contaminants. More specifically, such aspect may relate to an apparatus and a method that uses UV light to generate ozone, uses the ozone to destroy impurities in the air, and then uses UV light to destroy ozone so that damaging ozone does not contact the sensitive materials or surfaces being cleaned.

In another aspect, the invention relates to methods and assemblies for treating an atmosphere that has been exposed to a material within an enclosed space so as to remove impurities from the atmosphere. Such impurity removal may involve one or more of a treatment to sanitize, decontaminate, deodorize, condition and/or dry the atmosphere, for example. Such methods and assemblies may employ UV light to generate ozone, the ozone in conjunction with UV light to destroy impurities in the air, and then uses a catalytic decomposer to destroy ozone so that damaging ozone does not contact the sensitive materials or surfaces being cleaned. In one aspect, the invention employs an integral ozone fuse to help ensure the treated atmosphere does not contain levels of ozone above desired limits.

2. Discussion of Related Art

A wide range of sports equipment is designed and used to protect the human body from injury. Equipment pieces are relatively large, bulky, oddly shaped, fitted with straps, and difficult to wash and dry. In soccer, a player wears shin guards and ankle guards to protect the lower leg. In hockey, a player wears knee pads, a chest protector, elbow pads, gloves, a helmet and hockey pants. In football, a player wears shoulder pads, leg and hip pads, a helmet, a neck roll, elbow pads and gloves. Bicyclists and roller blade skaters use helmets. Many sports require general or specialized footwear, such as cleats, sneakers, spikes, skates, roller blades and the like. Workers can wear similar equipment.

Protective equipment can be worn with direct contact against a skin or a head surface. Whether the equipment directly contacts the human body or is separated by clothing or a piece of cloth, sweat soaks into materials, such as pads, elastic material, straps, foam, and other materials. If not properly dried or cleaned, the sweat-soaked equipment becomes a site for growth of bacteria, mold, mildew, fungus, and other microorganisms that can spread disease, cause odor and/or damage or discolor the equipment. The equipment and the bag, bin or other storage container can become malodorous. Odors from the equipment can emanate from or through the container and make unpleasant the corresponding room, such as a vehicle compartment. Merely blowing air across the equipment to dry the equipment can more broadly release odors from the evaporated sweat and moisture into the room, house or other compartment. It is desirable to have an apparatus and/or method for drying, deodorizing, and/or sanitizing equipment and/or its surrounding air or atmosphere, quickly and conveniently.

Known products in the marketplace have addressed this need. Dhaemers, U.S. Pat. No. 6,134,806 describes a portable sport equipment bag having an air distributor connected with a hose to a blower and an ozone generator operable to move pressurized air and ozone into the air distributor. The air distributor moves the air and ozone into the bag to dry the sports equipment contained within the bag, to destroy bacteria, molds and fungus in the bag. The ozone directly contacts the sports equipment, which can be a serious problem because ozone can destroy many equipment materials, such as when the ozone exists in air at concentrations that are high enough to kill undesirable microorganisms. When well mixed with contaminated air, ozone can more effectively and efficiently oxidize contaminants. Also, ozone is a lung irritant and can leak out of the equipment bag and dangerously be inhaled, such as when the user opens the sports equipment bag. These safety issues can be serious enough to warrant alternative approaches.

Dhaemers, U.S. Pat. No. 5,369,892 describes a dryer in the form of an armoire with an internal drying chamber for housing articles that are subjected to heated circulating air, to remove moisture from the articles. Ultraviolet lamps within the drying chamber destroy contaminants in the air and on the air conditioning coils, in the drying chamber. A similar configuration is taught by Liang, U.S. Pat. No. 5,152,077, which is limited because contaminated materials must be in a direct line of sight of a UV light source, in order to be sanitized. The clothes alone can restrict exposure between the material and the UV light. Air that circulates in the armoire cannot be deodorized.

There is a need for a convenient, efficient, cost effective and efficient method and apparatus for drying, deodorizing and/or sanitizing air and equipment, particularly without damaging the equipment.

Many other types of products can benefit from being dried, sanitized and deodorized, such as toys used at home or in commercial or institutional settings, including health care facilities, day care centers and/or schools. The materials used in toys and stuffed animals make it difficult to clean them quickly and conveniently. Many toys need to be individually wiped with disinfectant to clean their surfaces. Disinfectants and wipes can be used to clean toys. These cleaning procedures are time consuming and burdensome.

There is a need for a method and apparatus for drying, deodorizing, and/or sanitizing a variety of products, quickly, safely and/or effectively, with minimal physical or chemical impact to the products.

Ethylene gas ($C_2H_4$) accumulates during the transport and storage of fresh fruits and vegetables and thus causes a problem for commercial agriculture and consumers. Small amounts of ethylene, sometimes less than 1 ppm, can induce fruit ripening, and can produce undesirable flavors such as bitterness, colors, such as yellowing or browning, and textures, such as softening, and thus can increase susceptibility to disease. Certain fruits and vegetables naturally generate ethylene during a ripening cycle. Other fruits and vegetables are highly sensitive to the presence of ethylene, but may or may not actually produce ethylene. The table in FIG. 9 lists some fruits and vegetables and known ethylene production rates and sensitivities.

The amount of ethylene that produces undesirable amounts or characteristics varies with different fruits and vegetables, but ethylene concentrations in the range of 0.1-10 ppm can produce a significant effect. There is a need for a system that removes ethylene from the air within a fruit or vegetable storage container while not damaging the fruits or vegetables.

Because there is significant industry value in maintaining fresh fruits and vegetables during transportation and storage, some technologies have been researched, developed and commercialized to control ethylene. These conventional methods and their limitations are shown in the table of FIG. 10.

There is a need for an alternative approach to ethylene control that would be less expensive, consume less power, and require less space.

SUMMARY OF THE INVENTION

It is an object of the invention to provide an improved method and/or apparatus for treating an atmosphere exposed to a material within an enclosed space.

In one aspect there is provided an apparatus and method for oxidizing ethylene to carbon dioxide and water using UV-generated ozone.

In another aspect there is provided an apparatus and method for oxidizing ethylene to carbon dioxide and water using UV-generated ozone in conjunction with UV light.

It is another object of an aspect of the invention to produce ozone to destroy ethylene and then to dissociate the excess ozone back to oxygen, to maintain acceptable levels of ozone within a shipping or storage container, for example that carries fresh fruits and vegetables. According to one embodiment, at least a portion of the ethylene can be destroyed in each pass through a cleaning unit or apparatus in accordance with the invention so that the atmosphere in the storage container is cleaned by repeated circulation through the cleaning apparatus. As long as the rate of destruction of ethylene is higher than the rate of generation of ethylene in the storage container, the cleaning apparatus will reduce the ethylene levels to a desired steady-state level. By designing the cleaning apparatus to partially clean the atmosphere, and relying on recirculation of the atmosphere to reduce the contaminants to desired levels, the balance between system performance, volume and cost can be better optimized.

It is another object of an aspect of the invention to provide cost effective assemblies and/or methods for better ensuring that ozone is not released into the ambient air in unsafe levels or amounts such as through an automatic shutdown of the assembly if the ozone level in the exhaust reaches a preselected threshold level or sums to a specified, integrated level over a particular period of time.

According to one embodiment, ethylene can be oxidized in an ethylene control unit and/or in ambient air of the storage container, such as at a lower ozone concentration. This dual approach can maximize ethylene removal from the container air and/or the produce packages. This dual approach can also minimize negative effects of ozone concentrations in an air handling system or in the produce itself. UV-generated ozone can also be used to remove additional pathogens that can degrade produce quality, such as with certain fungus or mold spores. Such an apparatus and method can meet application requirements of a wide range of container sizes and refrigeration or other environmental control systems.

Such a method and system can generate, use, and destroy ozone, for example to remove ethylene and/or other impurities in the air or atmosphere within fresh fruit and vegetable containers. In one embodiment, ozone is both generated and destroyed by UV light rays. The ethylene removal apparatus and/or method can be accomplished with a wide variety of known configurations of storage containers, air flow patterns and/or refrigeration units.

According to such aspect of the invention, it is possible to dry, deodorize and sanitize materials and/or the air or atmosphere that surrounds the materials. The materials can be sports equipment stored in a sports bag or an equipment bin, toys stored in a toy box and/or fruits or vegetables stored in a refrigerator or produce storage container.

It is possible to clean, deodorize, and sanitize materials by circulating cleaned and conditioned air across the materials. The contaminants that are transferred from the materials to the air are treated in an air cleaning unit. The cleaned air is circulated back across the materials, such as in a convective manner. Air flow and/or heat can be used to drive the contaminants from the materials into the air. The contaminants can be, for example, moisture, volatile matter, such as odors, bacteria, spores, dirt, or other gases, liquids and/or microorganisms.

The contaminants that are driven into an air stream can be drawn into a compact, low-cost, effective cleaning unit where the contaminants are destroyed. The cleaned air can be re-circulated back to the storage container.

Also provided are a method and device to generate, use, and ultimately at least partially destroy the generated ozone for decontamination, deodorization, and/or conditioning of the air and/or the materials. The air cleaning unit can be positioned inside a chamber of various suitable configurations or designs. Air that requires treatment is drawn from the chamber into the cleaning unit, passes across an ozone generator, such as a UV bulb that emits light rays in the UV wavelength that generates ozone. In one embodiment it has been found that the combination of ozone and UV light serve to rapidly destroy contaminates within the cleaning unit. The clean air is then drawn across a second UV bulb that emits in the UV wavelength that destroys ozone. Alternatively, the treated air can be drawn across a catalyst to dissociate ozone to molecule oxygen. Clean, ozone-free air is then reintroduced to the storage chamber.

One or more additional treatment devices may be placed in the chamber to heat, dry, cool or dilute the air stream that circulates through the air cleaning unit.

There is also provided a method for at least one of sanitizing, decontaminating, deodorizing, conditioning and drying an atmosphere exposed to a material within an enclosed space. In accordance with one embodiment, such method involves circulating the atmosphere through an atmosphere treating unit. Ozone is generated within the atmosphere treating unit. The generated ozone mixes with the atmosphere in the atmosphere treating unit. The mixture of atmosphere and ozone is exposed to UV light in the atmosphere treating unit to remove at least a portion of the contaminants in the atmosphere. At least a portion of the ozone is removed from the UV light-exposed mixture of atmosphere and ozone to form an ozone-depleted containing an amount of ozone below a preselected threshold amount. The ozone-depleted mixture can then be appropriately exhausted into the enclosed space. At least a portion of the ozone-depleted mixture can be desirably recirculated through the atmosphere treating unit to remove at least a portion of the contaminants remaining in the ozone-depleted mixture. The exhausting and recirculating steps can be repeated until the ozone-depleted mixture exhausted into the enclosed space contains an amount of the contaminants below a preselected threshold amount.

The system of this invention, which includes the apparatus and/or the method, can produce ozone to destroy contaminants and then used to dissociate the excess ozone back to oxygen in order to maintain appropriate levels of ozone within the storage container. The system of this invention provides a number of significant benefits compared to existing technology.

Circulation of air and ozone in the presence of UV light through a well designed unit can be more efficient at cleaning the air as compared to injecting gaseous ozone, at non-hazardous levels, into still or calm air or other ambient conditions. It appears that at low concentrations of ozone, random encounters with contaminants results in too slow of a process of contaminant removal. The reaction of ozone with ethylene or other organic gases is greatly enhanced in the presence of UV light. However, there can be significant benefits to combining both of these methods to maximize benefits obtained from the use of ozone.

This invention provides two opportunities to oxidize the odors and the microorganisms, one in an air cleaning unit, and the second, such as at a lower ozone concentration, in the ambient air of the storage container. This dual approach can better remove impurities from the air in the storage container and from surfaces of the materials. Ozone concentrations are relatively high in the air cleaning unit and the mixing rates between the ozone and the air is relatively high, and thus the oxidation rates of the impurities is relatively high. The air in the storage container can be quickly deodorized and sanitized. The concentration of ozone at the exit of the air cleaning unit can be precisely established. A very low concentration of ozone can be established in the storage container in order to sanitize surfaces of the materials, such as over a longer period of time. This dual approach can minimize negative effects of ozone concentrations in the air handling system or the surface of the sports or other equipment.

BRIEF DESCRIPTION OF THE DRAWINGS

The above and other features and objects of this invention are better understood from the following detailed description taken in view of the drawings wherein:

FIG. 8 is table showing ozone-generating ultraviolet light performance parameters;

FIG. 9 is a table showing ethylene production and sensitivity of selected produce;

FIG. 10 is a table showing conventional ethylene control technologies and corresponding limitations;

FIG. 11 is a graph showing a reduction of ozone using ultraviolet light, according to one embodiment of this invention;

DETAILED DESCRIPTION OF THE INVENTION

Throughout this specification and in the claims, the terms air cleaning unit and atmosphere treating unit are intended to relate to an apparatus for sanitizing, decontaminating, deodorizing, conditioning, drying and/or otherwise treating, cleaning, modifying and/or improving an atmosphere within a container.

Figure 1:
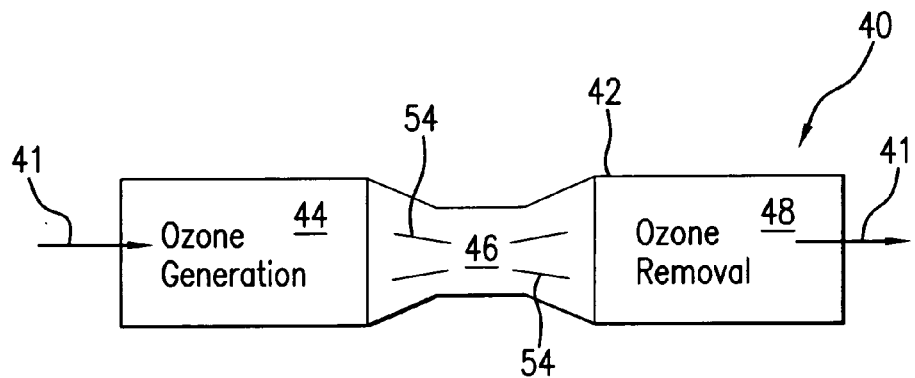
FIG. 1 is a diagrammatic view showing three elements of an air cleaner, including an ozone generation zone, a mixing zone and an ozone dissociation zone, according to one embodiment of this invention.
Figure 2:
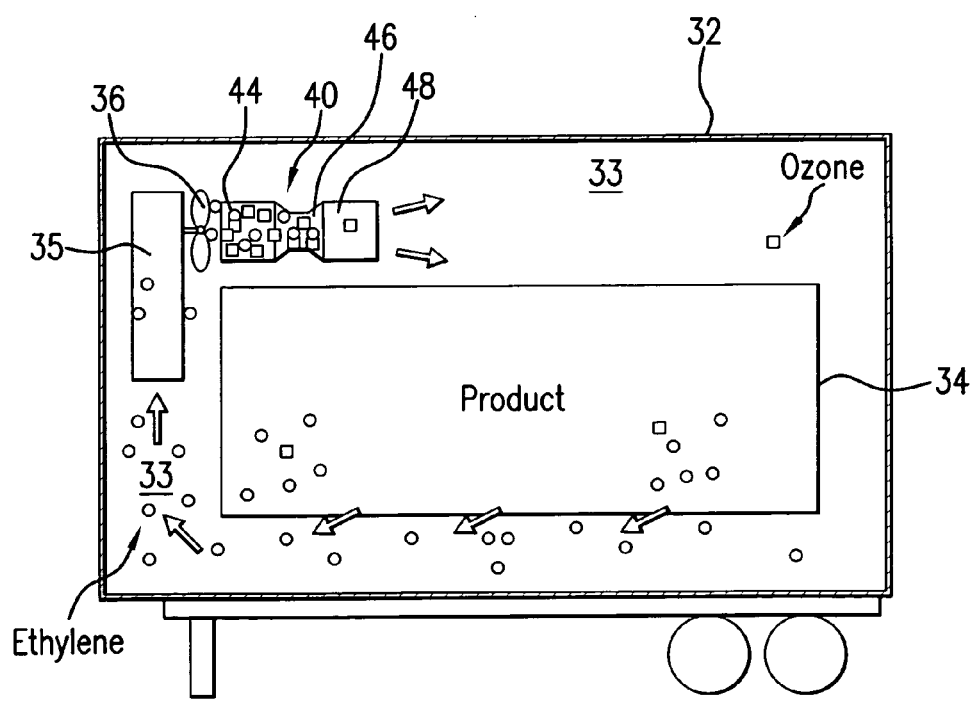
FIG. 2 is a diagrammatic showing of an inside of a container, such as a refrigerated truck trailer, a housing and an evaporator, an air cleaner, and a material or product, according to one embodiment of this invention.
Figure 3:
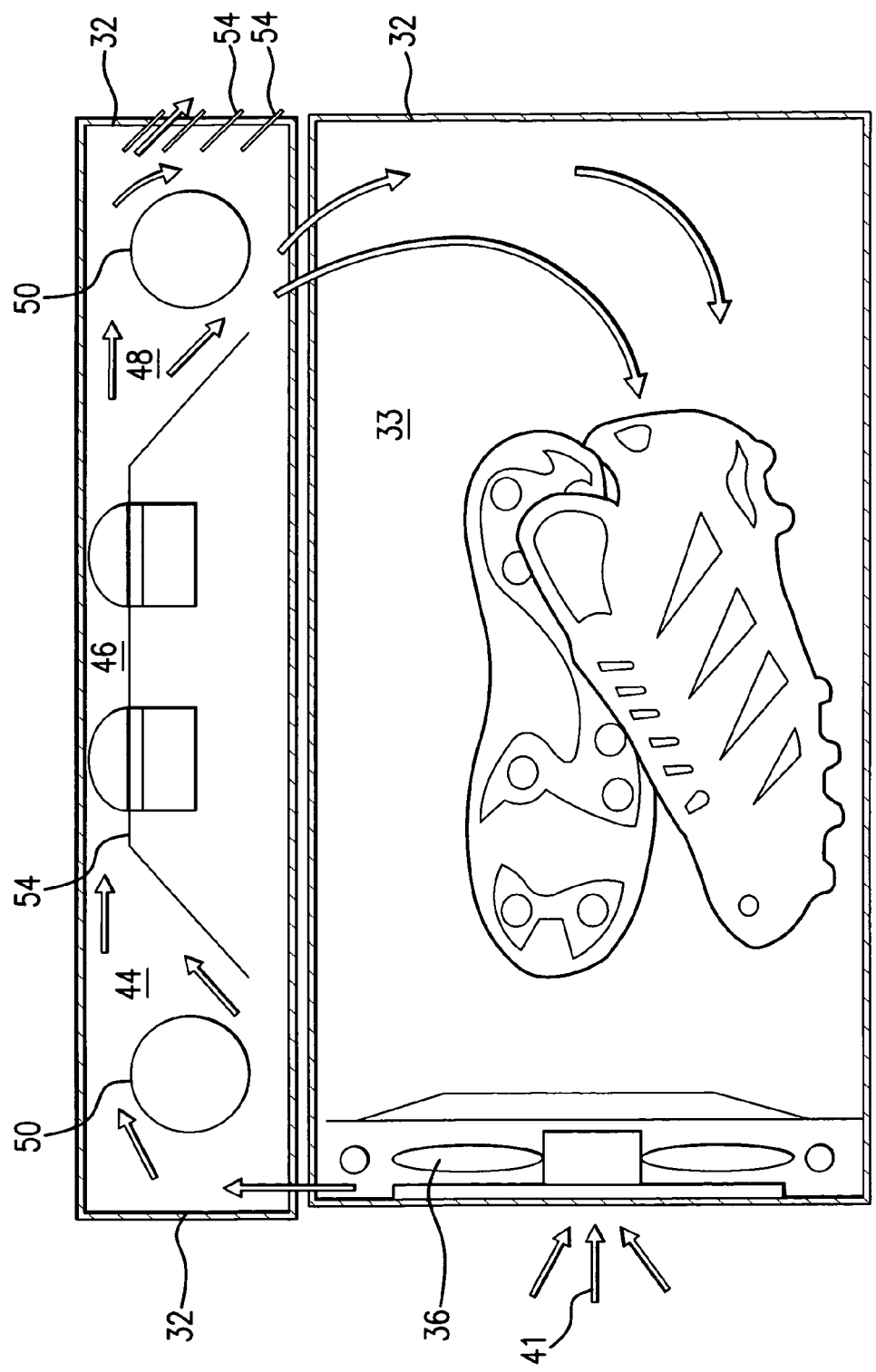
FIG. 3 is a diagrammatic side view of a cylindrical configuration of an air cleaner unit, according to one embodiment of this invention.
Figure 4:
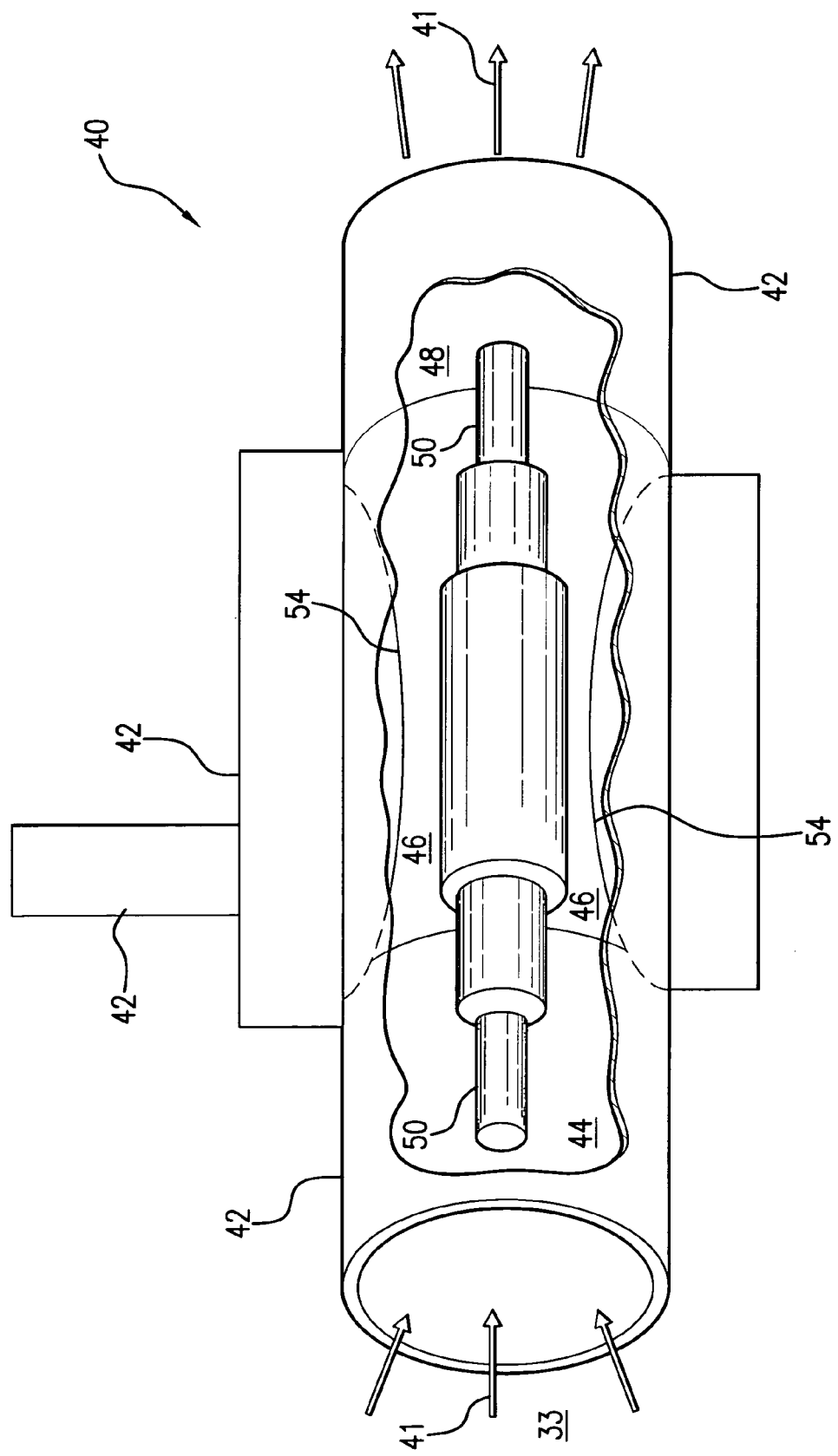
FIG. 4 is a diagrammatic partial sectional view of an air cleaner unit, according to one embodiment of this invention.
Figure 5:
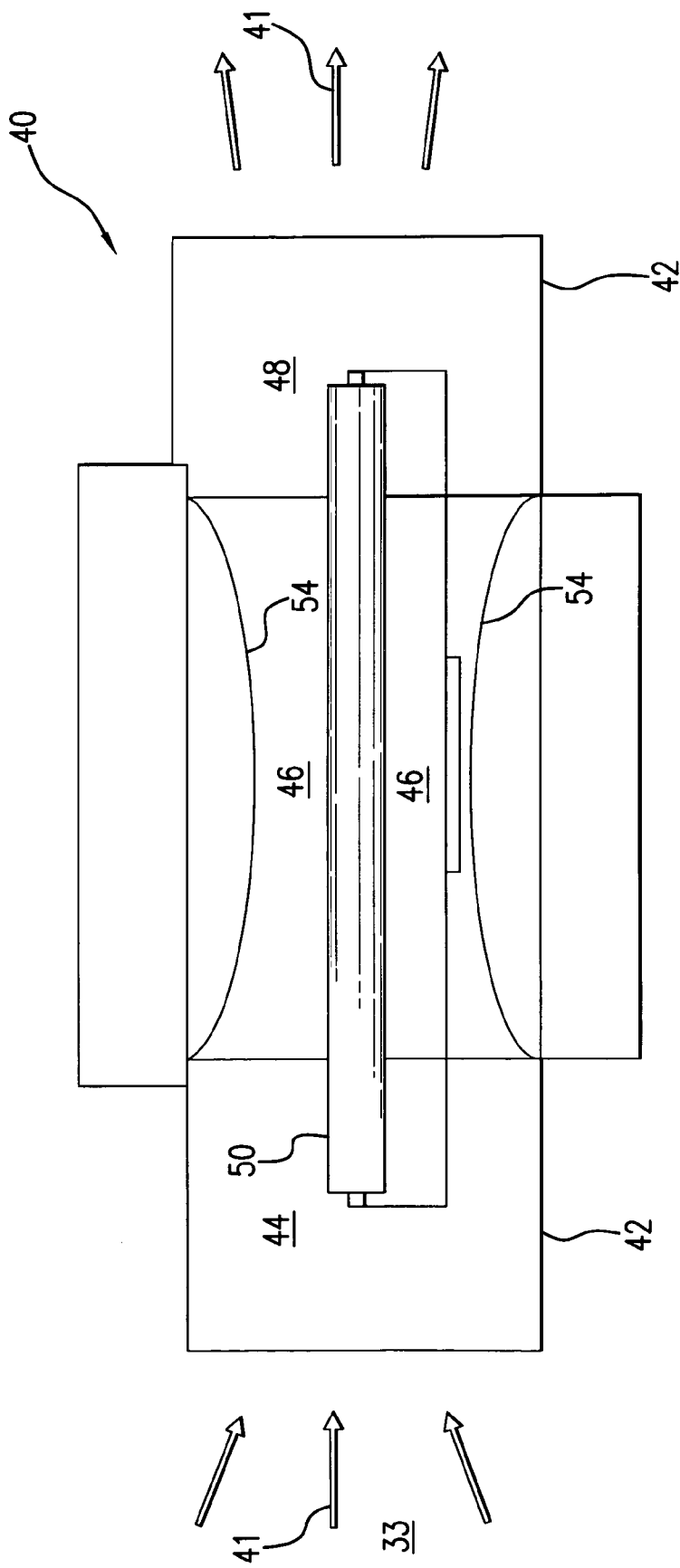
FIG. 5 is a diagrammatic partial sectional view of an air cleaner unit, according to another embodiment of this invention.
Figure 6:
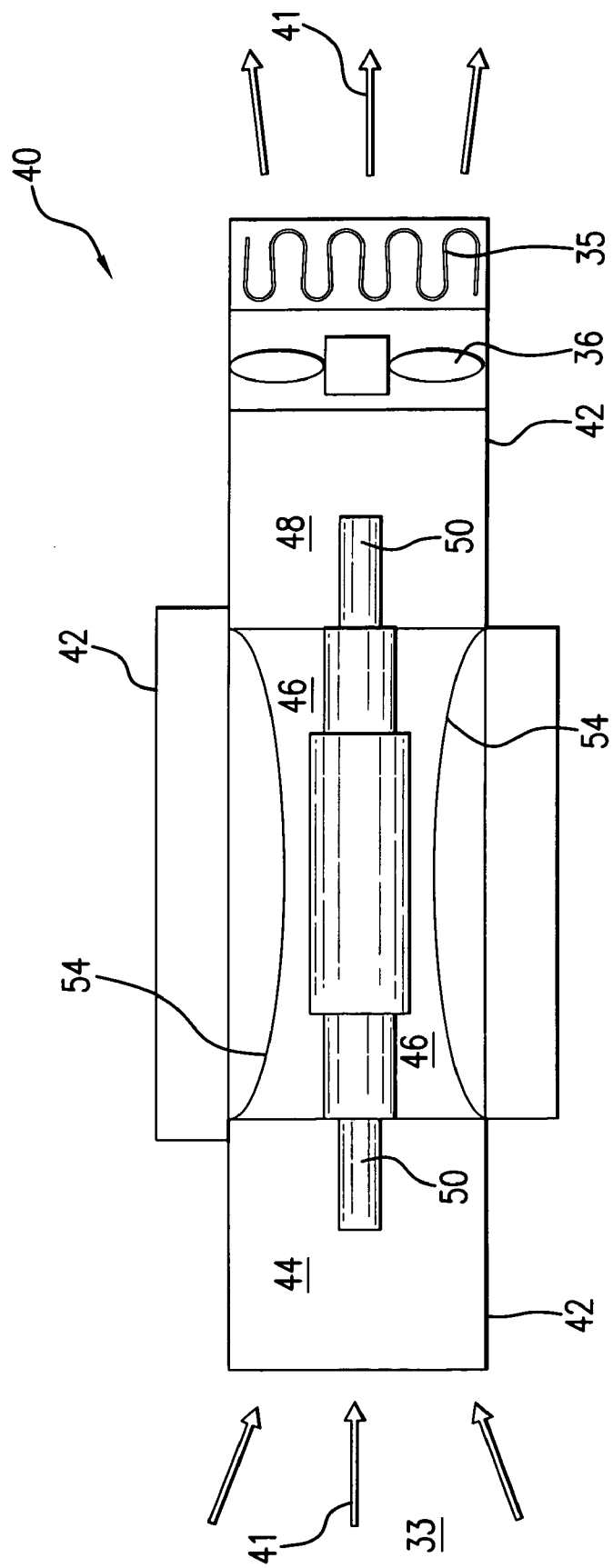
FIG. 6 is a diagrammatic partial sectional view of an air cleaner unit, according to one embodiment of this invention.
Figure 7:
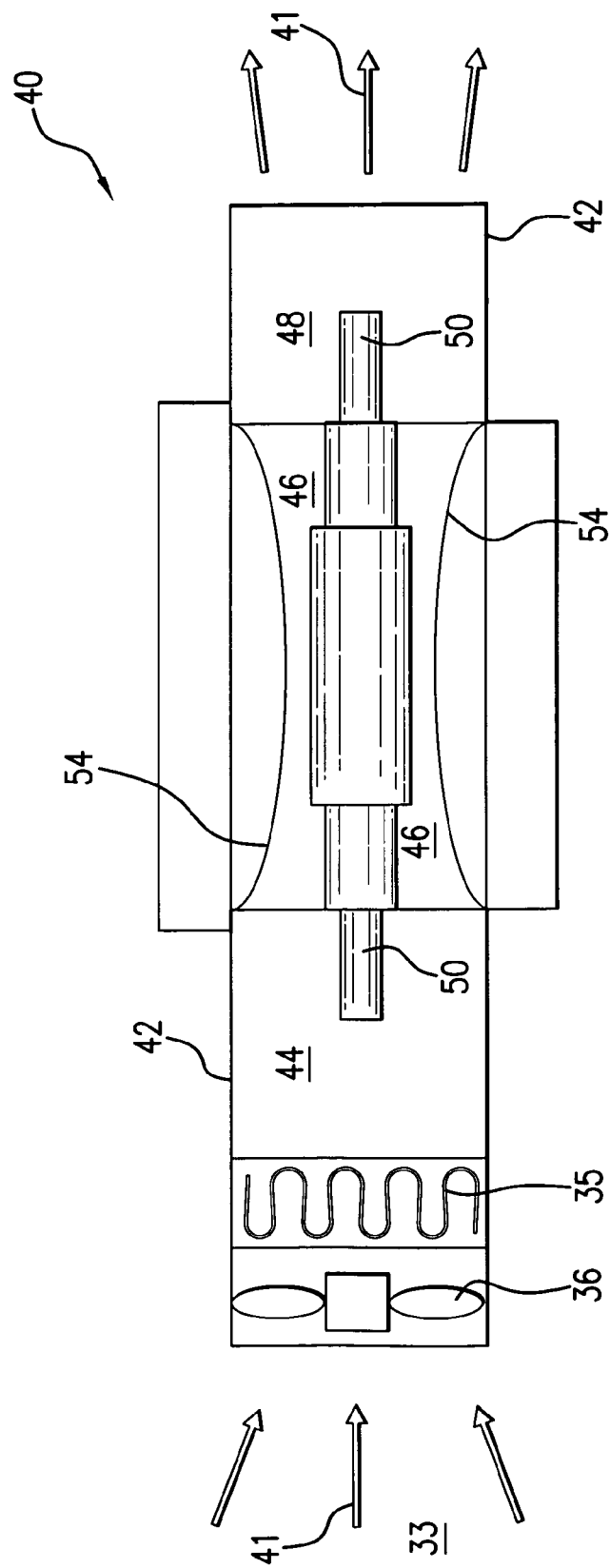
FIG. 7 is a diagrammatic partial section view of an air cleaner unit, according to one embodiment of this invention.

FIG. 1 shows air cleaning unit 40, according to one embodiment of this invention. FIG. 2 shows air cleaning unit 40 positioned or mounted within container 32, such as a truck trailer, according to one embodiment of this invention. FIG. 3 shows air cleaning unit 40 positioned or mounted within a different container 32, according to another embodiment of this invention.

As shown in FIG. 1, air cleaning unit 40 has structure 42, such as a housing, that forms zone 44, zone 46 and zone 48. As air or another suitable atmosphere passes through air cleaning unit 40, such as shown by the arrows of flow direction 41, in FIG. 1, atmosphere 33 passes first through zone 44, then through zone 46, and then through zone 48.

In certain embodiments according to this invention, ozone is generated within atmosphere 33 passing through zone 44.

The generated ozone is mixed with atmosphere 33, through zone 46. As described in greater detail below, in embodiments wherein ethylene is an atmosphere contaminant that is desired to be removed, zone 46 can desirably serve for both ozone mixing and reaction with ethylene.

At least a portion of the generated ozone is removed from the mixed atmosphere, within zone 48. Thus, as the atmosphere discharges from zone 48, the atmosphere has been exposed to generated ozone, mixed with the generated ozone and then disassociated from at least a portion of the generated ozone.

FIGS. 4-7 each shows a different embodiment of air cleaning unit 40, according to this invention. As shown in FIGS. 4-7, UV source 50 comprises a light bulb with an ultraviolet output and/or a corona discharge device that generates ozone within zone 44. Any other suitable mechanical, electro-mechanical and/or other device can be used to generate ozone within zone 44.

FIGS. 1 and 2 show zone 48 downstream with respect to zone 46, and zone 46 downstream with respect to zone 44. In other embodiments according to this invention, zone 46 which is the mixing zone can be at least partially within or part of zone 44 where ozone is generated. In other embodiments according to this invention, zone 48 in which ozone is removed can be at least partially within or part of zone 46, in which mixing occurs. In other embodiments according to this invention, mixing, such as in zone 46, can occur entirely throughout zones 44 and/or 48.

FIG. 1 shows flow diverter 54 positioned within zone 46. In other embodiments according to this invention, flow diverter 54 can be mounted within or exposed to zone 44 and/or zone 48. Flow diverter 54 can be any suitable device that mixes fluid flowing through air cleaning unit 40, including but not limited to a flow nozzle, a baffle, a structure, a mechanical mixer and/or a nozzle, such as a nozzle forming a plurality of flow channels.

As shown in FIGS. 1 and 4-7, for example, mixing can occur by forming a nozzle that has a variable diameter along a flow direction of the atmosphere flowing through air cleaning unit 40. Any suitable venturri nozzle or other converging and/or diverging nozzle can be used to mix the fluid flow.

Figure 12:
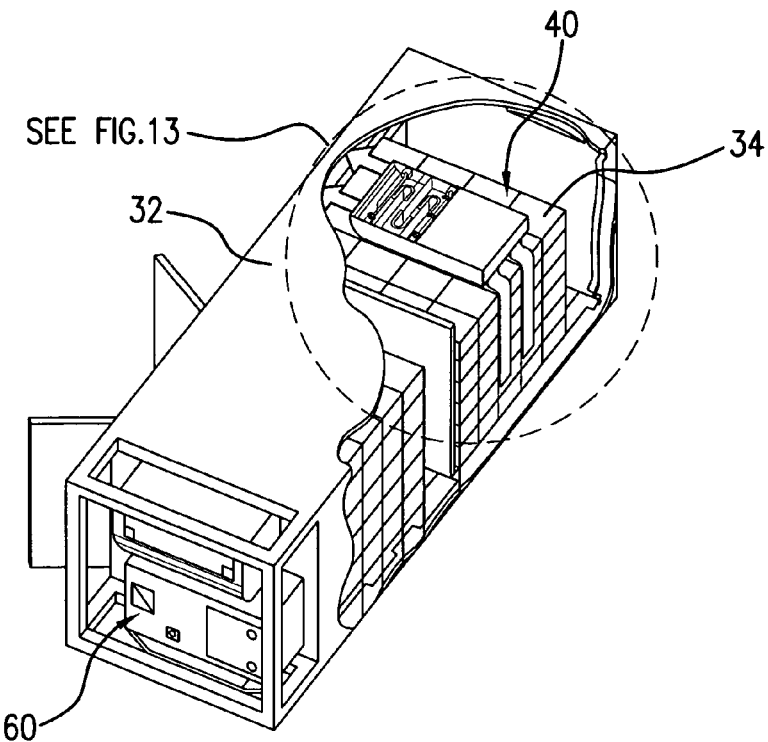
FIG. 12 is a partial cut-away perspective view of an air cleaning unit mounted within a container, according to one embodiment of this invention.
Figure 13:
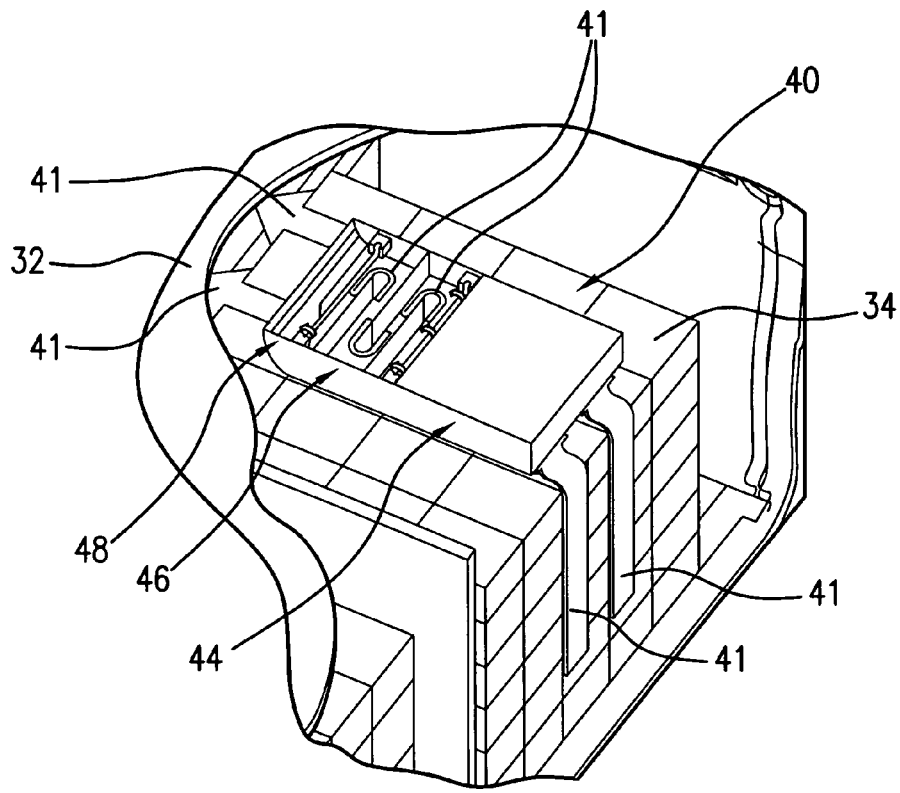
FIG. 13 is an enlarged perspective view showing a partial cut-away section of an air handling unit, according to the embodiment as shown in FIG. 12.

FIGS. 12 and 13 show another embodiment for mixing fluid flowing through air cleaning unit 40. The arrows in FIG. 13 show flow direction 41 along which fluid passes through zone 44, zone 46 and zone 48 of air cleaning unit 40. FIG. 13 shows one particular baffle arrangement. However, any other suitable baffle configuration and design can be used to mix the fluid flow.

Figure 14:
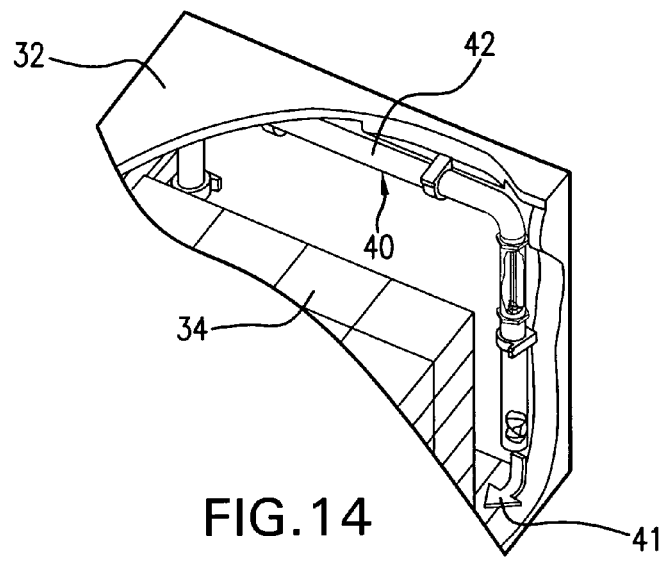
FIG. 14 is a partial cut-away perspective view of an air cleaning unit mounted within a container, according to another embodiment of this invention.
Figures 15, 16:
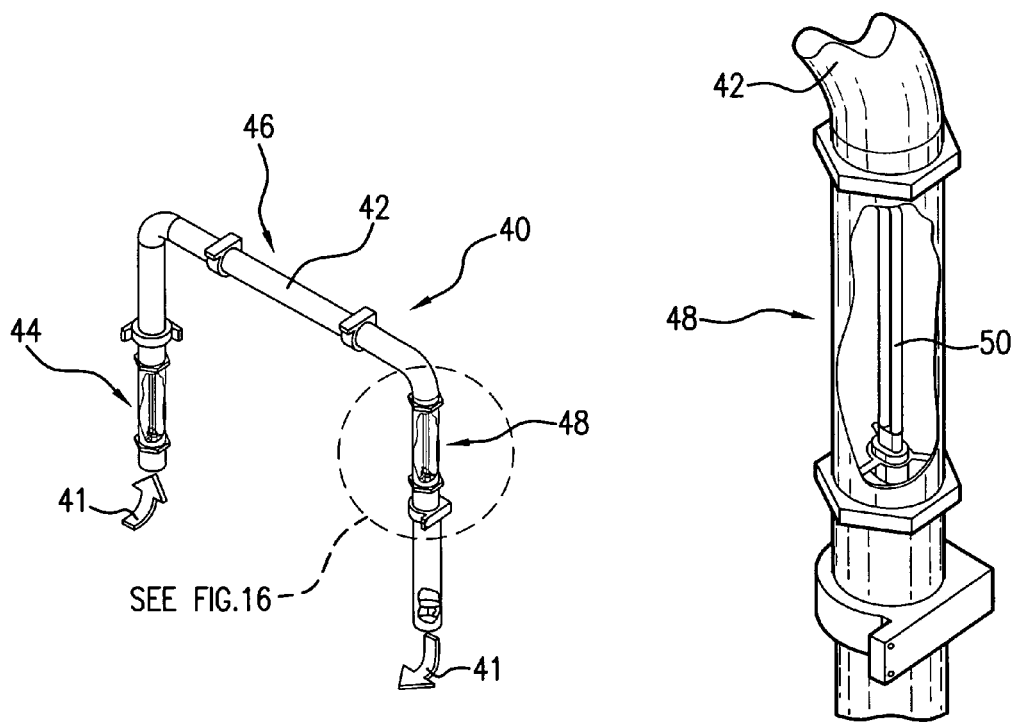
FIG. 15 is a partial cut-away perspective view of an air cleaning unit, according to the embodiment shown in FIG. 14.
FIG. 16 is an exploded partial cut-away perspective view of an ozone removal section, according to one embodiment of this invention.

FIGS. 12 and 13 show one embodiment of air cleaning unit 40 positioned within container 32 which stores or houses material 34. FIGS. 14-16 show another embodiment of air cleaning unit 40 according to this invention. FIG. 14 shows air cleaning unit 40 mounted within container 32.

FIG. 15 shows structure 42 formed by tubular structural members, for example. Any suitable blower or air moving unit, such as an axial fan and/or a centrifugal blower, can be used to draw fluid into an inlet and discharge fluid through an outlet, for example in flow direction 41 as shown in FIG. 15. Structure 42 as shown in FIGS. 15 and 16 may or may not include flow diverter 54, depending upon the particular intended use and requirements for operation.

FIG. 16 shows UV source 50, for example shown as a light bulb in FIG. 16, that can be used to remove ozone within zone 48. Zone 48 can be positioned as shown in FIG. 15 or in any other suitable position for accomplishing ozone removal or reduction.

Air cleaning unit 40 can be constructed with structure 42 as described in this specification and/or with any other suitable structure that can house or form any zone or chamber used to accomplish ozone generation, mixing and/or ozone removal.

As shown in FIGS. 12-16, structure 42 can be or form an independent apparatus or system that can be positioned within container 32 and/or exposed to atmosphere 33. With an independent arrangement or a stand-alone arrangement of air cleaning unit 40, it is possible to operate air cleaning unit 40 independently of any existing air conditioner 35. For example, an independent system can accommodate flow rates passing through air cleaning unit 40 which are different than flow rates passing through air conditioner 35, such as an existing refrigeration unit mounted within a transport trailer or other container.

Any suitable conventional device for removing ozone can be mounted within or exposed to zone 48. In certain embodiments according to this invention, ozone can be removed or disassociated from zone 48 with a thermal decomposer, a combustible support, a catalytic decomposer (for example, CARULITE® 200, manganese dioxide/copper oxide catalyst, and/or activated carbon), a photo-disassociating device and/or an ultraviolet light source.

In certain embodiments according to this invention, the UV light is generated at a wavelength of about 187 nm to absorb oxygen and thus produce ozone, such as within zone 44. In certain embodiments according to this invention, the UV light is generated at a wavelength of about 254 nm to absorb the ozone and cause photolysis or photo-disassociation. FIG. 11 is a graph showing ozone reduction with ultraviolet light at about 254 nm.

Figure 17:
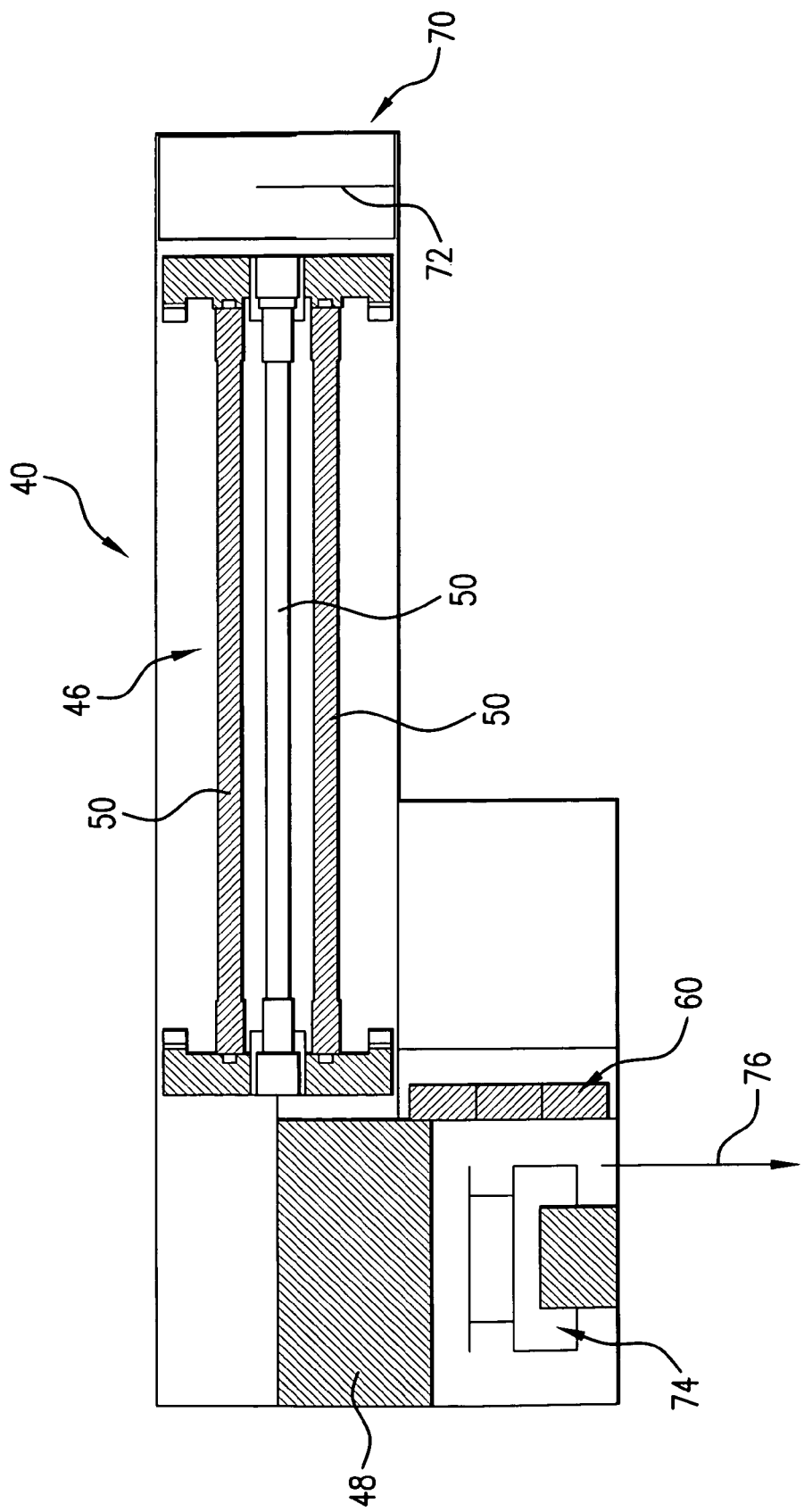
FIG. 17 is a simplified sectional side view of an atmosphere treatment assembly, according to another embodiment of the invention.
Figure 18:
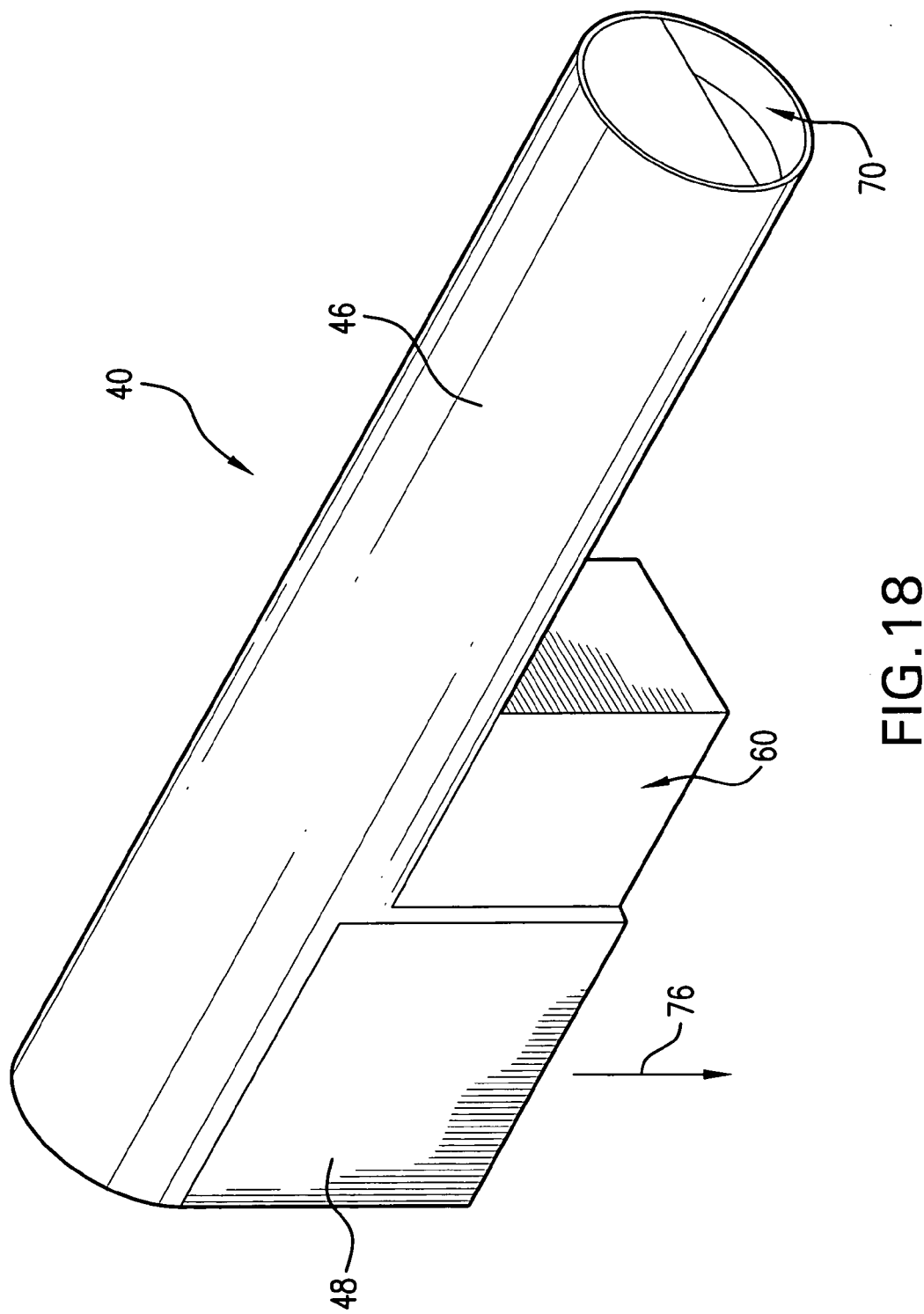
FIG. 18 is a simplified perspective view of the atmosphere treatment assembly shown in FIG. 17.

FIGS. 17 and 18 illustrate a more compact version of an atmosphere treating unit 40 in accordance with one embodiment. In this configuration, air or another suitable selected atmosphere enters via inlet 70 and passes around light baffles 72 and through unit 40. Four UV bulbs 50 (three of which are visible in FIG. 17) are located in zone 46 where ozone is generated and ethylene is rapidly destroyed in the presence of UV light. Ozone is removed through the catalytic decomposer in zone 48. A fan pulls the atmosphere through unit 40. Controls 60 are provided and can communicate or transmit signals through a wired and/or a wireless connection to control any operating parameter and/or function of unit 40. The overall volume of this atmosphere treating/air cleaning unit is less than 1 cubic foot.

As will be appreciated by those skilled in the art and guided by the teachings herein provided, light baffles or other suitable design features can desirably be incorporated into atmosphere treating units to minimize and/or avoid exposure to UV light external to the unit.

Figure 19:
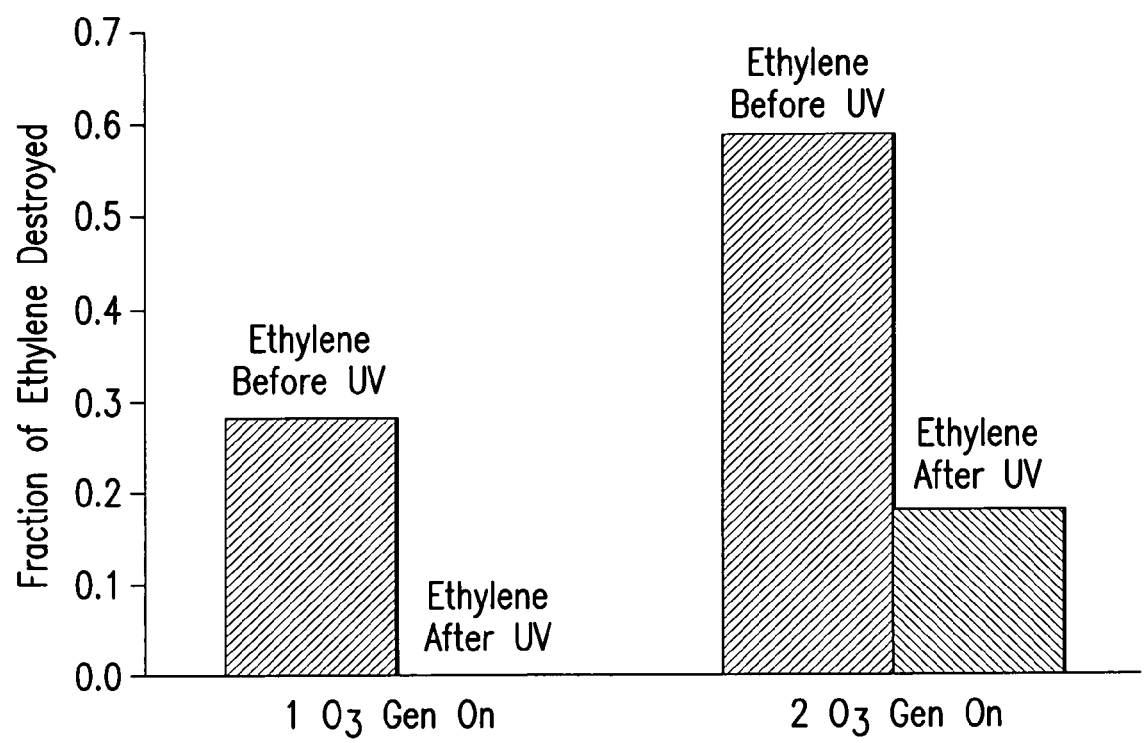
FIG. 19 is a chart showing that UV light exposure in the reaction zone significantly improves performance, e.g., enhances the reaction rate of ozone and ethylene, according to an embodiment of the invention.

The destruction of ethylene is greatly enhanced in a configuration in which the ozone is oxidizing the ethylene in the presence of UV light. An experiment was conducted in which UV bulbs were used to generate ozone. In one test, the ethylene was added to the system upstream of the UV lights so that the ethylene would mix with the ozone laden air in the presence of the UV bulbs. In a second test, the ethylene was added to the system downstream of the UV bulbs so that there was no view factor of the reacting gases and the UV light itself. This experiment was conducted twice: once with one UV bulb energized and again with two UV bulbs energized. FIG. 19 shows the difference in ethylene destruction rate between these two test conditions. With one UV bulb energized, the fraction of ethylene destroyed was over 25% in the presence of UV light and almost 0% without the light present. With two UV bulbs energized, the fraction of ethylene destroyed was about 60% in the presence of UV light and less than 20% without the UV light enhancing the reaction rate. This experiment demonstrates that the presence of UV light significantly enhances the reaction rate of ozone and ethylene.

As shown in FIGS. 2 and 3, for example, an outlet of structure 42 which forms air cleaning unit 40 is in communication with zone 48 and atmosphere 33 or the space of container 32. As shown in FIGS. 2 and 3, material 34 is mounted, positioned or otherwise housed within container 32 so that material 34 is exposed to atmosphere 33.

Also shown in FIGS. 2 and 3, air mover 36 can be used to circulate atmosphere 33. Any suitable fan or other air moving device can be used to create flow of atmosphere 33 through air cleaning unit 40. As shown in FIG. 2, air conditioner 35, such as an evaporator or any other suitable air conditioning device, is mounted within atmosphere 33 of container 32.

Container 32 can comprise any suitable structure that defines a chamber or other suitable space for accommodating material 34. Container 32 can be formed by a transportation trailer, a storage trailer, a storage bin, a bag, a shipping container, an equipment bin and/or an expandable structure.

In certain embodiments according to this invention, the method for sanitizing, decontaminating, deodorizing, conditioning, drying or otherwise treating atmosphere 33 begins with generating ozone within atmosphere 33 passing through zone 44. Within zone 46, the generated ozone is mixed with the atmosphere 33 to enhance removal of undesirable contaminates or other elements of atmosphere 33. At least a portion and possibly the entire amount of generated ozone is removed from the mixed atmosphere 33 as it passes through zone 48.

It is possible to mix atmosphere 33 with the generated ozone within zone 44 and/or zone 46. It is possible to continue to mix atmosphere 33 with the generated ozone as it passes through zone 48.

The apparatus of this invention can comprise a control unit, for example located at the exit of the evaporator. The control unit can comprise three sections, including a UV-light (187 nm) ozone generation chamber for generating a relatively high ozone concentration, a mixing zone for removing ethylene with ozone, and a UV-light (254 nm) ozone dissociation chamber for destroying ozone to a level desired for the atmosphere in the container.

The apparatus and/or the method of this invention can comprise a controller or other suitable control system for managing or controlling ozone generation, mixing and/or ozone removal.

In some embodiments of this invention, a controller, such as control 60 as shown in FIG. 19, can communicate or transmit signals through a wired and/or a wireless connection to control any operating parameter and/or function of air cleaning unit 40. In some embodiments of this invention, control parameters are based on timing functions of one or more UV sources 50. It is possible to control the apparatus and/or the method to achieve desired results without requiring, for example, a relatively expensive ethylene sensor and/or a feedback loop. Any control based on timing functions of UV source 50, according to this invention, can be relatively inexpensive and will require reduced maintenance and reduced replacement parts, particularly as compared to a sensor-based control system.

In certain embodiments of this invention, the controller can comprise a transport and storage mode and/or a cleaning mode. In the transport and storage mode, air cleaning unit 40 can cycle with an evaporator. When an evaporator air handler operates, two sets of UV sources 50 can be energized to remove any residual ethylene from atmosphere 33. An override mode can start air mover 36 or any other suitable air handler, for example to begin moving air through the evaporator and/or air cleaning unit 40, for a defined or chosen time period. The controller can then trigger the air handler to start and begin passing fluid through air cleaning unit 40, even if a thermostat or other sensor does not request or call for the evaporator to start.

In certain embodiments of this invention, during the cleaning mode, container 32 can be closed, with or without a lock and/or an alarm, during a cleaning cycle. During the cleaning cycle, UV source 50 or another suitable ozone generator can be energized while fluid passes through air cleaning unit 40, such as for any preset and/or calculated time period. After a defined or calculated time period for generating ozone is reached, UV source 50 can be stopped or not operated while air is circulated through air cleaning unit 40, for example for a time that is sufficient to expose atmosphere 33 and thus kill or remove molds, fungus, spores and/or any other undesired contaminate. Any necessary time period can be calculated from a program of the controller and/or from known data. After the defined and/or calculated time period, UV source 50 can be started within zone 48 to remove ozone from the fluid flowing through air cleaning unit 40. This same function can be achieved with the use of a catalytic decomposer as an alternative to the UV source 50 in zone 48. With the use of a catalytic decomposer to destroy the ozone in zone 48, the cleaning cycle would utilize a bypass of zone 48 during the cleaning mode that would allow ozone build-up in the storage container. After the defined and/or calculated cleaning period, the bypass would be closed and UV light 50 in zone 44 would be turned off. The circulation of atmosphere through the catalytic decomposer in zone 48 would clean the atmosphere in storage container of ozone.

After the cleaning cycle time period expires, the controller can signal and/or activate to open any lock and/or to deactivate any alarm. The controller can also be used to communicate with and learn information from any suitable sensor that detects a desired parameter or when the ozone concentration is at a certain level, such as when the ozone concentration falls below a level defined by any government agency and/or other guideline recommendation.

According to this invention, a test facility to conduct ozone generation, ethylene removal and ozone destruction testing can include the following components: instrumentation, including a Thermo Fisher 49i ozone analyzer, a storage control systems electro-chemical ethylene analyzer, voltage and/or current meters to monitor a power draw of lamps or UV source 50; an ozone generator, including a UV lamp G24T6VH/U ozone generator (180 nm wavelength, 25 Watts, 2.3 grams/hour output); an ozone remover, including a UV lamp G24T6/U germicidal lamp (254 nm wavelength, 25 Watts, 8.5 Watts UV output); and a stainless steel model container and flow system, including a container sized at 1/8 scale, flow rates scaled to achieve up to 1 air change per minute, an axial fan positioned in a duct to move air through zones 44, 46 and 48, and high vacuum stainless steel weld fittings to provide leak-free operation.

Figure 20:
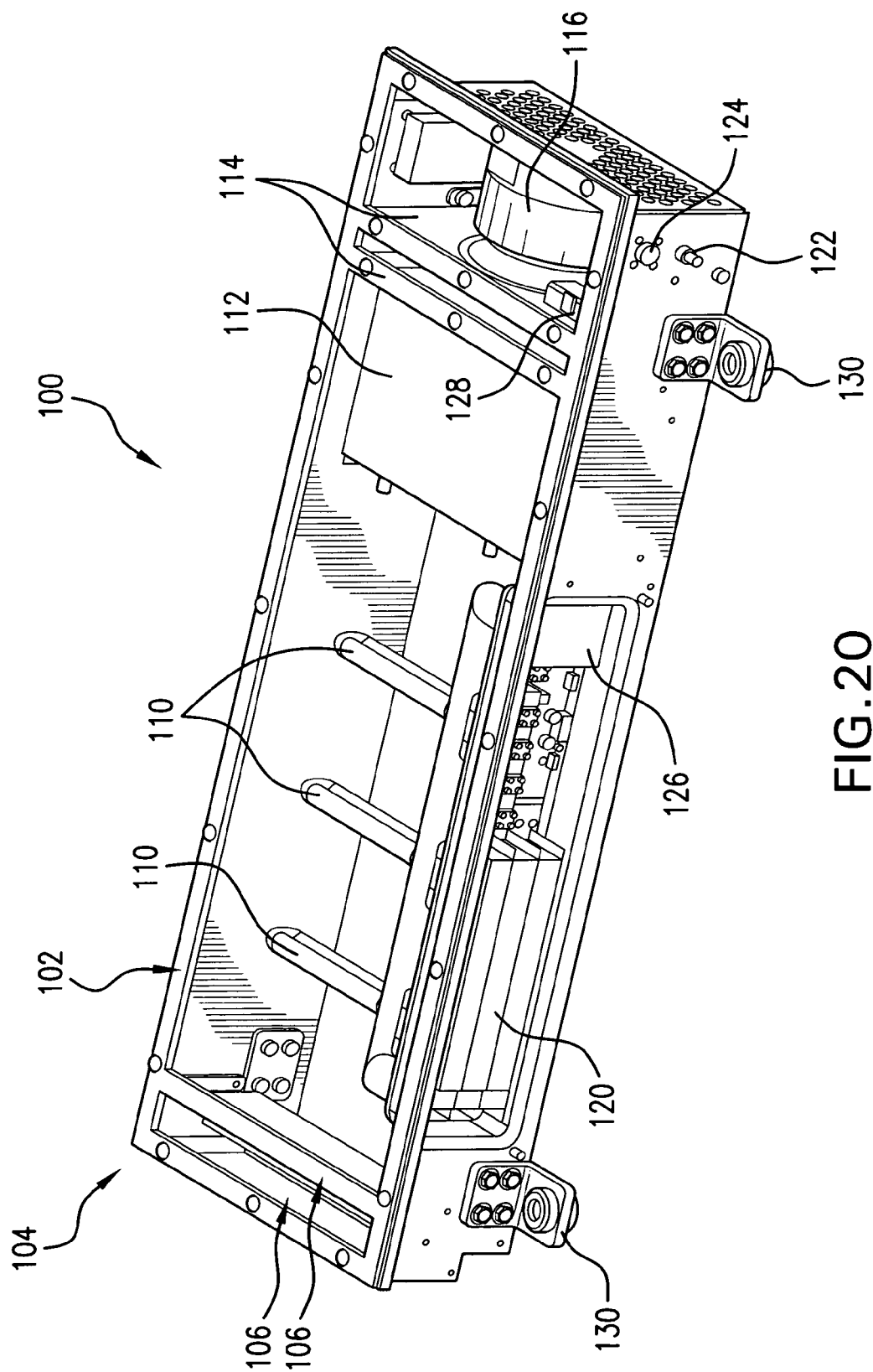
FIG. 20 is a simplified schematic view showing elements of an assembly in accordance with one aspect of the invention.
Figure 21:
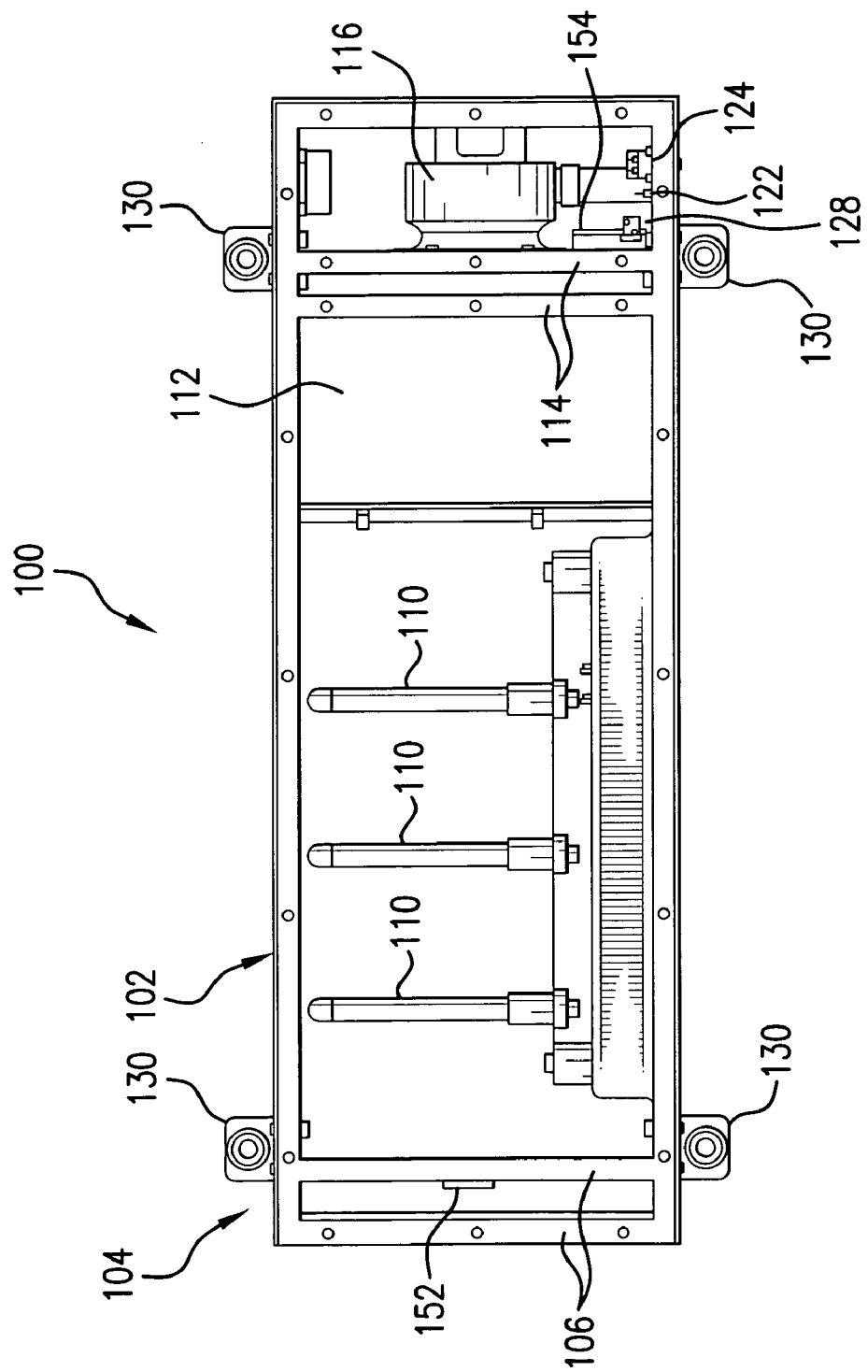
FIG. 21 is a top view of the assembly shown in FIG. 20, showing two possible locations of an ozone fuse in accordance with one aspect of the invention.
Figure 22:
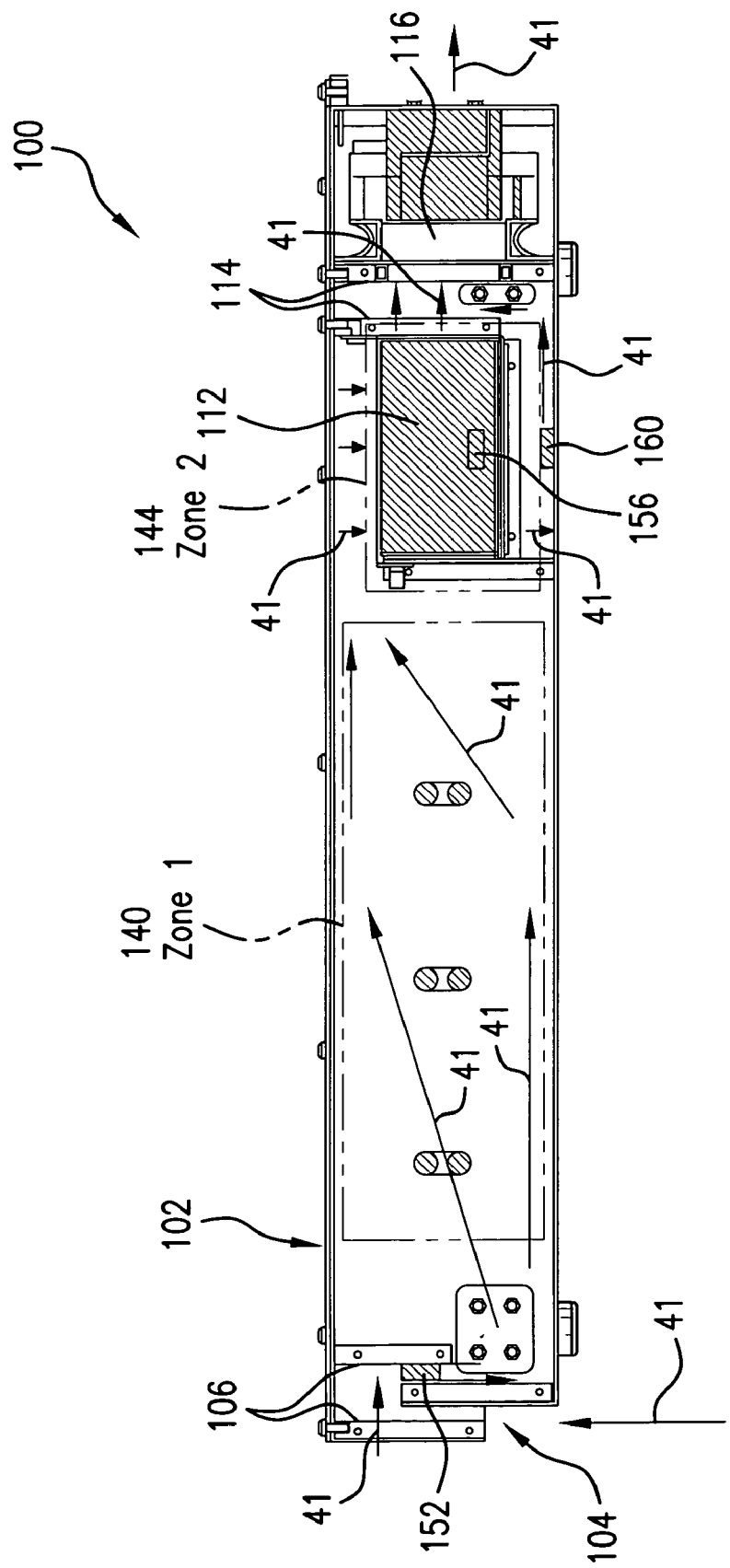
FIG. 22 is a side view with a cut-away of the assembly shown in FIG. 20, indicating three possible locations for an ozone fuse in accordance with one aspect of the invention.

Turning now to FIGS. 20-22 there is illustrated assembly 100 and, in particular, atmosphere treating unit structure 102 in accordance with one aspect of the invention. Atmosphere treating unit structure 102 includes: air inlet 104; light baffles 106 (to ensure that no viewing angle would result in external exposure to UV light); UV light bulbs 110 that generate ozone; catalytic ozone destruction bed 112; a set of flow baffles 114 and fan 116 to pull air through structure 102; and various control elements useful in the operation of assembly 100, including bulb ballasts 120, on-off switch 122, system operation indicator 124, microprocessor 126 and safety switch 128, for example. Assembly 100 also includes suitable mounting elements or features such as shock absorbing mounts 130.

Thus, atmosphere treating unit structure 102 includes first zone 140 in which ozone is generated within the atmosphere and exposed to UV light, and second zone 144 in which at least a portion of the generated ozone is removed from the mixed atmosphere to form an ozone-depleted mixture. First zone 140 and second zone 144 are generally represented by respective zone boxes, shown via phantom lines in FIG. 22. Those skilled in the art and guided by the teachings herein provided will understand and appreciate that such depiction of the zones is not intended to necessarily limit the size, shape or dimensions of the zones or the placement or positioning of the zones. Furthermore, as for example herein described, such zones relative to each other, may be separated, adjacent or overlap, in whole or in part, as may be appropriate or desired for a particular application.

In such structure, UV light bulbs 110, used to generate ozone and to irradiate ozone mixed with the atmosphere, are oriented perpendicularly to atmosphere flow through the structure.

In particular embodiments, it can be desirable to expose the mixture of atmosphere and ozone to UV light of either 185 or 254 nm wavelength at an input rate of 0.5 watt per cfm to 10 watts per cfm, where such input rates or ratios reflect power into the UV bulb(s) divided by the total flow rate through the system/unit.

Assembly 100 may include one or more shut-off devices 150 in operational communication with structure 102 to shut-off atmosphere treatment assembly 100 when a selected ozone level parameter exceeds a preselected amount. One or more shut-off devices 150 can be variously located within or about assembly 100. For example, FIG. 21 illustrates a first possible location, designated by reference 152, in air inlet region 104 and a second possible location, designated by reference 154 downstream of catalytic ozone destruction bed 112. FIG. 22, in addition to location 152 also shows possible location 156 within catalytic ozone removal bed 112 and location 160, downstream of catalytic ozone removal bed 112. The arrows in FIG. 22 show flow direction 41 along which fluid passes through the unit assembly 100.

Suitable such shut-off devices may be in the form or nature of a fuse, e.g., an integral ozone fuse such as can automatically shut down assembly operation if and when the fuse is blown. For example, a chemical input such as a level or amount of ozone triggers an electrical switch or fuse such as to shut down operation of the assembly such as by turning off the UV light bulbs.

Figure 23:
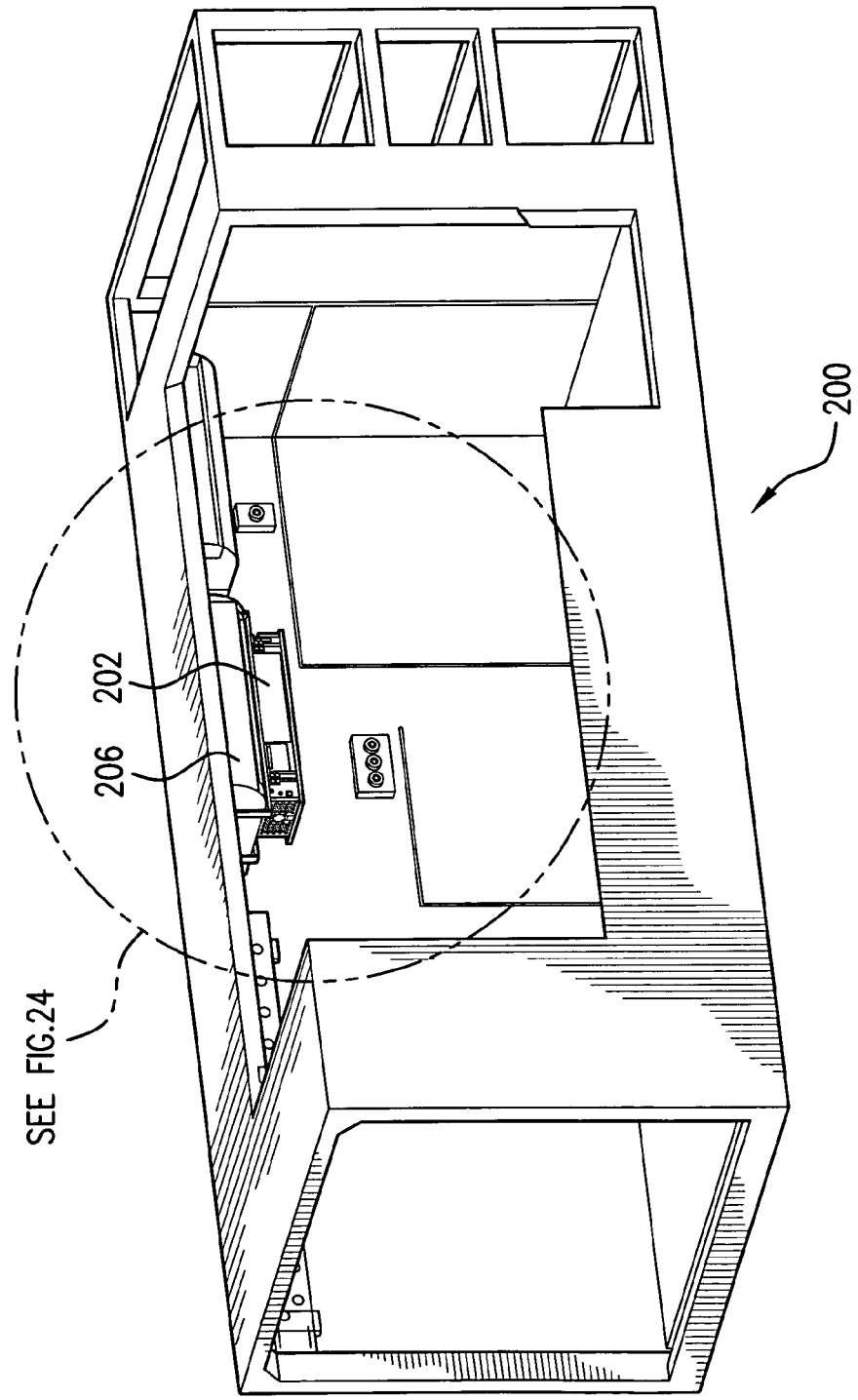
FIG. 23 is a partially cut-away view of an enclosed space, such as a refrigerated truck trailer, operationally associated with an atmosphere treatment assembly in accordance with one embodiment of the invention.
Figure 24:
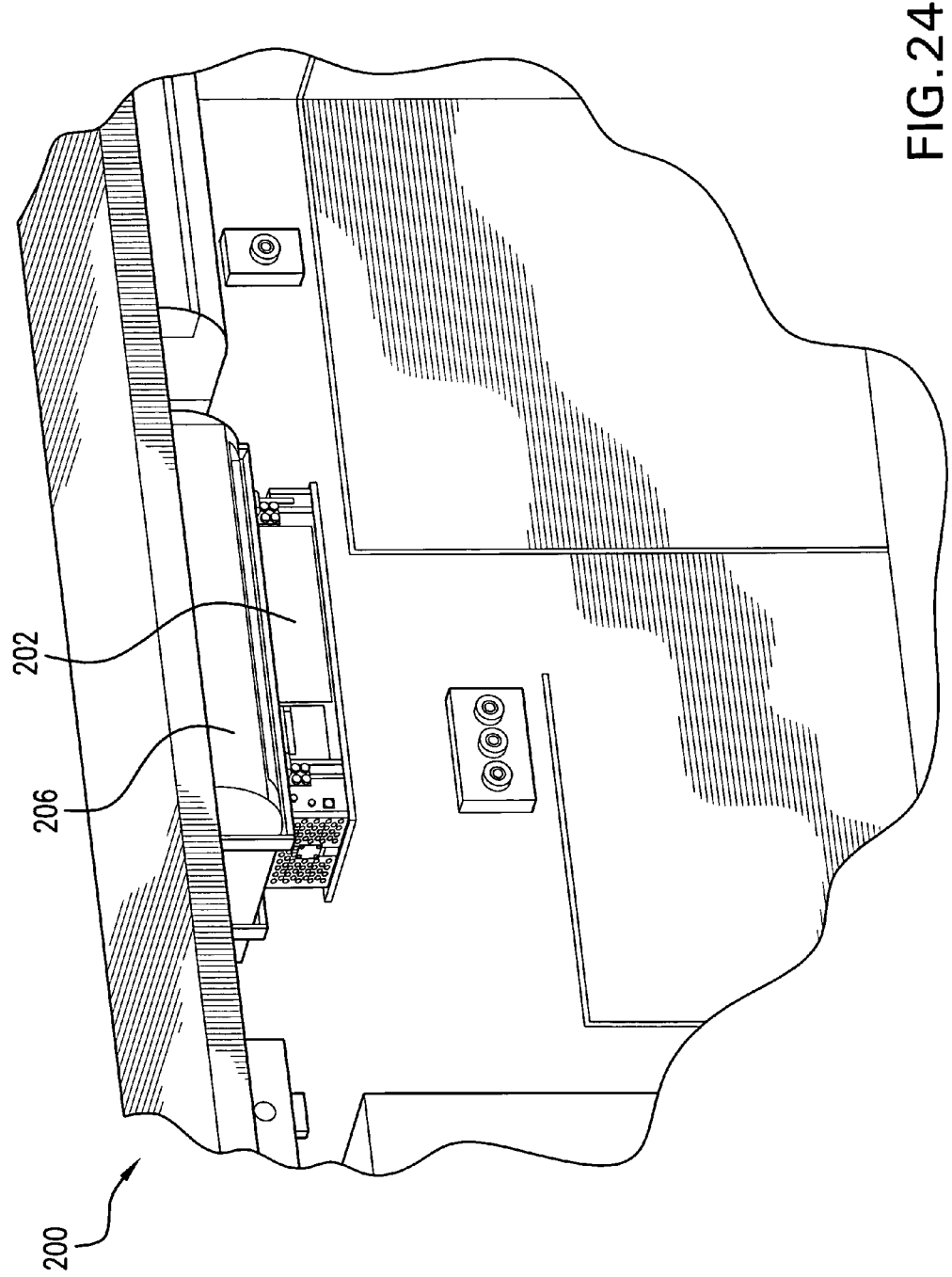
FIG. 24 is an enlarged perspective fragmentary view showing a partial cut-away of an enclosed space operationally associated with an atmosphere treatment assembly, according to the embodiment as shown in FIG. 23.

FIGS. 23 and 24 are partially cut-away views of enclosed space 200, such as a refrigerated truck trailer, operationally associated with atmosphere treatment assembly 202 in accordance with one embodiment of the invention.

Enclosed space 200 can be normally used to carry or convey one or more products (not shown), with atmosphere treatment assembly 202 used to treat the atmosphere held or otherwise contained within the enclosed space.

Enclosed space 200 also houses or contains evaporator 206 such as may be utilized to control the humidity or moisture level within the enclosed space 200.

Those skilled in the art and guided by the teachings herein provided will appreciate that, in accordance with one embodiment, the atmosphere in a storage container can desirably be cleaned via repeated circulation through a treatment or cleaning unit, such as herein described. For example, in the case of desired removal of ethylene from a selected atmosphere, at least a portion of the ethylene can be destroyed in each pass through the unit. As long as the rate of destruction of ethylene is higher than the rate of generation of ethylene in the storage container, the cleaning apparatus will reduce the ethylene levels to a desired steady-state level. By designing the cleaning apparatus to partially clean the atmosphere on a per pass basis, and relying on recirculation of the atmosphere to reduce the contaminants to desired levels, the balance between system performance, volume and cost can be better optimized. For example, by utilizing such recirculation, the amount of power or energy required for proper operation of the unit can be significantly reduced or minimized such as by reducing the number of UV lights required to be energized in any particular pass of atmosphere to be treated through the unit.

While in the foregoing detailed description this invention has been described in relation to certain preferred embodiments thereof, and many details have been set forth for purposes of illustration, it will be apparent to those skilled in the art that this invention is susceptible to additional embodiments and that certain of the details described herein can be varied considerably without departing from the basic principles of this invention.

What is claimed is:

1. A method for at least one of sanitizing, decontaminating, deodorizing, conditioning and drying an atmosphere exposed to a material within an enclosed space, the method comprising:
    circulating a flow of the atmosphere containing a contaminant through an atmosphere treating unit; Passing the flow through a light baffle at a viewing angle to contain UV light in the atmosphere treating unit;
    generating ozone within the reaction zone;
    mixing generated ozone with the contaminants in the flow in the reaction zone;
    exposing a mixture of the contaminants in the flow and the ozone to UV light in the reaction zone to remove at least a portion of the contaminants in the flow;
    removing at least a portion of the ozone from the flow in a removal zone downstream of the reaction zone by catalytically decomposing the ozone with a catalyst comprising manganese dioxide and copper oxide to form an ozone-depleted mixture containing an amount of ozone below a preselected threshold amount; and
    exhausting the ozone-depleted mixture into the enclosed space.

2. The method according to claim 1, additionally comprising:
    recirculating at least a portion of the ozone-depleted mixture through the atmosphere treating unit to remove at least a portion of the contaminants remaining in the ozone-depleted mixture.

3. The method according to claim 1, wherein ozone is generated with at least one of an ultraviolet light source and a corona discharge device.

4. The method according to claim 1, wherein the generating of ozone is within a generation zone, the exposing of the mixture of atmosphere and ozone to UV light is within a reaction zone, and the reaction zone is at least one of within the generation zone and downstream of the generation zone.

5. The method according to claim 1, wherein the removing of at least a portion of the ozone from the UV light-exposed mixture of atmosphere and ozone is within a removal zone, the exposing of the mixture of atmosphere and ozone to UV is within a reaction zone, and the reaction zone is at least one of within the removal zone and upstream of the removal zone.

6. The method according to claim 1, wherein the mixture of atmosphere and ozone are exposed to UV light of either 185 or 254 nm wavelength at an input rate of 0.5 watt per cfm to 10 watts per cfm.

7. The method according to claim 1, wherein the removing of at least a portion of the ozone from the UV light-exposed mixture of atmosphere and ozone comprises removal of the ozone by at least one of thermally decomposing ozone, absorbing and reacting ozone on a combustible support, and photo-disassociating ozone with an ultraviolet light source.

8. The method of claim 7, wherein the removing of at least a portion of the ozone from the UV light-exposed mixture of atmosphere and ozone is monitored via an ozone fuse whereby ozone presence in the exhausted ozone-depleted mixture in an amount greater than preselected results in shut-down of the atmosphere treating unit.

9. The method according to claim 1, wherein the ozone-depleted mixture contains at least a portion of the generated ozone.

10. The method according to claim 1, wherein the atmosphere is at least one of heated, cooled, dried and diluted.

11. The method according to claim 1, wherein a controller operates at least one parameter corresponding to at least one of the generating, mixing, exposing and removing steps.

12. An atmosphere treatment assembly for implementing the method of claim 1.

13. The atmosphere treatment assembly according to claim 12, additionally comprising:
    a first conveyance assembly for conveying the atmosphere from the enclosed space into the structure; and
    a second conveyance assembly for conveying at least a portion of the ozone-depleted mixture to the enclosed space.

14. The atmosphere treatment assembly according to claim 12, wherein at least one of an ultraviolet light source and a corona discharge device generates the ozone within the first zone.

15. The atmosphere treatment assembly according to claim 12, wherein with respect to a flow direction of the atmosphere through the structure, the second zone is at least one of within the first zone and downstream of the first zone.

16. The atmosphere treatment assembly according to claim 12, wherein with respect to a flow direction of the atmosphere through the structure, the second zone is at least one of within the third zone and upstream of the third zone.

17. The atmosphere treatment assembly according to claim 12, wherein at least one of a flow nozzle, a baffle, a mechanical mixer, and a nozzle forming a plurality of flow channels, is at least one of mounted within and exposed to the second zone.

18. The atmosphere treatment assembly according to claim 12, wherein UV light bulbs are used to generate ozone and to irradiate ozone mixed with the atmosphere and wherein the UV light bulbs are oriented perpendicularly to atmosphere flow through the structure.

19. The atmosphere treatment assembly according to claim 12, wherein at least one of a thermal decomposer, a combustible support, a catalytic decomposer, a photo-disassociating device and an ultraviolet light source is at least one of mounted within and exposed to the third zone.

20. The atmosphere treatment assembly according to claim 12, wherein an outlet of the structure forms communication between the third zone and the enclosed space.

21. The atmosphere treatment assembly according to claim 12, wherein the enclosed space is one of a transportation trailer, a storage trailer, a storage bin, a bag, a shipping container, an equipment bin and an expandable structure.

22. The atmosphere treatment assembly according to claim 12, further comprising a controller operating at least one parameter corresponding to at least one of the ozone generation, mixing and removal.

23. The atmosphere treatment assembly according to claim 12, wherein an ultraviolet light source generates at least one of ultraviolet light at about 187 nm within the first zone and ultraviolet light at about 254 nm within the third zone.

24. A method for at least one of sanitizing, decontaminating, deodorizing, conditioning and drying an atmosphere exposed to a material within an enclosed space, the method comprising:
    circulating a flow of a contaminant-containing atmosphere through an atmosphere treating unit;
    passing the flow through a light baffle at a viewing angle to contain UV light in the atmosphere treating unit;
    generating ozone within a reaction zone of the atmosphere treating unit;
    changing a flow direction of the flow in the reaction zone to uniformly mix the generated ozone in the contaminant-containing atmosphere within the reaction zone;
    exposing the flow throughout the reaction zone to UV light;
    oxidizing at least a portion of contaminants from the mixture of the contaminant-containing atmosphere and the ozone by exposing the mixture to the UV light to increase an oxidation reaction rate in the reaction zone of the atmosphere treating unit;
    removing the ozone from the mixture of contaminant-reduced atmosphere and the ozone in an ozone-removal zone downstream of the reaction zone to form an ozone-depleted mixture containing an amount of ozone below a pre-selected threshold amount; and
    exhausting the ozone-depleted and contaminate-reduced atmosphere into the enclosed space.

25. The method according to claim 24, wherein a catalyst within the ozone-removal zone is of a manganese dioxide/copper oxide.

26. The method according to claim 24, wherein the contaminant is ethylene.

27. A method for at least one of sanitizing, decontaminating, deodorizing, conditioning and drying an atmosphere exposed to a material within an enclosed space, the method comprising:
    circulating a flow of the atmosphere containing a contaminant through an atmosphere treating unit;
    passing the flow through a light baffle and containing the UV light in the atmosphere treating unit;
    generating ozone within a reaction zone of the atmosphere treating unit;
    passing the flow and changing a flow direction of the flow between an air inlet of the atmosphere treating unit and an exit from the reaction zone and causing a uniform mixture of the ozone in the contaminant-containing atmosphere within the reaction zone;
    exposing the flow throughout the reaction zone to UV light;

oxidizing the contaminants from a mixture of the contaminant-containing atmosphere and the ozone by exposing the mixture to the UV light to increase an oxidation reaction rate in the reaction zone of the atmosphere treating unit;

irradiating with the UV light in the reaction zone of the atmosphere treating unit the mixture of contaminant-containing atmosphere and the ozone and killing at least a portion of microbiological contaminants from the mixture;

removing the ozone from a mixture of a contaminant-reduced atmosphere and the ozone in an ozone-removal zone downstream of the reaction zone to form an ozone-depleted mixture containing an amount of ozone below a pre-selected threshold amount; and exhausting an ozone-depleted contaminant-reduced atmosphere into the enclosed space.

28. The method according to claim 27, wherein a catalyst within the ozone-removal zone is of a manganese dioxide/copper oxide.

29. The method according to claim 27, wherein a flow rate of the flow through the atmosphere cleaning unit is in a range from about 0.5 cfm to about 150 cfm.

* * * * *